United States Patent [19]
Wolfstieg

[11] Patent Number: 4,691,334
[45] Date of Patent: Sep. 1, 1987

[54] X-RAY EXAMINATION APPARATUS

[75] Inventor: Ulrich M. E. A. Wolfstieg, Bad Herrenalb, Fed. Rep. of Germany

[73] Assignee: U.S. Philips Corporation, New York, N.Y.

[21] Appl. No.: 659,799

[22] Filed: Oct. 11, 1984

[30] Foreign Application Priority Data

Oct. 12, 1983 [EP] European Pat. Off. ........... 83201456

[51] Int. Cl.$^4$ .......................................... G01N 23/207
[52] U.S. Cl. ...................................... 378/71; 378/79; 378/81
[58] Field of Search ..................... 378/71, 72, 73, 79, 378/81

[56] References Cited

U.S. PATENT DOCUMENTS

| 2,829,262 | 4/1958 | Hamacher | 378/79 |
| 3,322,948 | 5/1967 | Baak et al. | 378/79 |
| 3,440,419 | 4/1969 | Gupta et al. | 378/71 |
| 3,852,594 | 12/1974 | Paolini | 378/73 |
| 4,128,762 | 12/1978 | Nagao et al. | 378/72 |

FOREIGN PATENT DOCUMENTS

| 0068045 | 1/1983 | European Pat. Off. | 378/73 |
| 0072050 | 5/1982 | Japan | 378/81 |
| 1089975 | 11/1967 | United Kingdom | 378/81 |

OTHER PUBLICATIONS

*IBM Technical Disclosure Bulletin,* vol. 11, No. 12, May 1969, pp. 1728–1729, B. S. Berry and R. Feder, "X-Ray Diffractometer for Thin Films".

Primary Examiner—Janice A. Howell
Assistant Examiner—D. Porta
Attorney, Agent, or Firm—Paul R. Miller

[57] ABSTRACT

A detector slit for $\theta$ rotation in an X-ray examination apparatus utilizing the Seemann-Bohlin focusing principle is suspended on a mechanical arm which is capable of rotating about a shaft through the center of the focusing circle. The Seemann-Bohlin system is for $\psi$ adjustment tiltable about an axis through an irradiated area on an object to be examined. The readjustment of the detector during the $\theta$ rotation is controlled by a device which provides detector rotation with with a 1:2 gear wheel transmission. For automatic limitation of a $\theta$ path to be chosen, the detector housing comprises an abutment pin which cooperates with switching elements connected to the mechanical arm. The X-ray tube has a construction reduced length and is connected to a high-voltage source via a rotatable right-angled connector.

15 Claims, 4 Drawing Figures

X-RAY EXAMINATION APPARATUS

The invention relates to an X-ray examination apparatus comprising an X-ray source and an X-ray detector which are arranged to be rotatable about an area to be irradiated on a specimen to be examined.

An apparatus of this kind is known as an X-ray stress measuring device from "Advances in X-ray Analysis Vol. 20, 1977, pages 369–377. An apparatus described therein utilizes a measuring method which is known as $\psi$ diffractometry. A summary of the differences with respect to and the advantages over the more customary $\omega$ diffractometry is stated on page 374 of this article.

There is a growing interest in the measurement of residual stresses in materials, notably in measurements which can be performed directly on machines, workpieces and the like. Knowledge of residual stresses may be of substantial assistance in tracing the causes of, for example, fractures due to metal fatigue, deformation or fissuring and the like. Such measurements can also indicate ways to avoid such faults by modification of the stress pattern or by reduction of the residual stresses, for example, by using a different manufacturing process. A better knowledge of the stresses in structure parts of, for example, machines such as roller bodies or ball bearings may be of assisitance in perfecting these parts by adaptation of the actual stress pattern as well as possible to the pattern which is a theoretical optimum for given properties. X-ray examination is up to now the only known non-destructive method having a resolution being high enough to obtain significant measuring results concerning residual stresses in materials.

Known apparatus of this kind often encounter problems in practice which restrict the measurements, notably in regard to the accessibility of product areas which are important for measurements. Moreover, the known apparatus are comparatively heavy and hence non-portable, notably when use is made of an X-ray tube having a high output, even though ease of transport and a high X-ray intensify are extremely important for fast measurements. It is a further drawback of many of the known apparatus that measurements can be performed only over a limited $\theta$ angular range and only a quantitative analysis can be performed. An increase of this angular range can offer a valuable contribution for determining phenomena such as the local composition of phases in alloys for example of retained austenite in hardened steel.

It is the object of the invention to mitigate the described drawbacks; to this end, an X-ray examination device of the kind set forth in accordance with the invention is characterized in that, utilizing Seemann-Bohlin Focussing, in an arrangement of the X-ray tube the irradiated area and the detector situated in a focussing plane, the detector and the X-ray source are rotatable about a mechanical shaft with a $\theta$-axis extending through the center and transversely to the Seemann-Bohlin focussing plane; in that during rotation the detector and a primary beam of the X-ray tube aim continually at the irradiated area and in that for $\psi$ inclination, the Seemann-Bohlin arrangement is rotatable about an axis which is in the focussing plane tangentially to the focussing circle through the center of the irradiated area.

Because an apparatus in accordance with the invention utilizes the Seemann-Bohlin radiation focussing principle, the detector and the X-ray source rotation can be performed by means of a real shaft, while a free scanning center is maintained. This highly benefits the stability and hence directly the accuracy of the measurement. Contrary to the customarily used arched guides, an exact and simple displacement for the $\theta$ movements are thus possible. Moreover, this construction enables the desired enlarged range of $\theta$ movements.

It is to be noted that Seemann-Bohlin focussing is known per se from German Ausleggungschrift No. 1,245,164; However, therein it is combined with an extremely complex detector movement, so that the advantages in accordance with the invention are not achieved. In the apparatus described therein, which is of the stationary type diffractometer for examination of only relatively small samples, the need for a free scanning center does not exist.

In one embodiment for the Seemann-Bohlin arrangement in accordance with the invention only the detector is driven by a motordrive, such as a stepping motor or a d.c. motor while the focus point of the X-ray tube can be moved by hand for orientation onto a choosen Bragg-angle. In a further embodiment the detector and the X-ray tube are provided with a motor driven mechanism such that both are moved in an opposite sense of rotation.

For the $\psi$ displacement of the radiation source in a preferred embodiment there is provided an arched guide on which the Seemann-Bohlin arrangement can be moved by means of, for example, a stepping motor or a d.c. motor. Because its positioning is far less critical, the pivoting of the source by means of an arched guide does not involve the drawbacks applicable to the rotation of the detector. The influence of the variation of $\psi$ on the accuracy of the measuring results is substantially smaller. Actually, the only requirement to be satisfied is that the irradiated area should remain positioned on the focussing circle. The $\psi$ motion can also be provided by an axis located outside the diffractometer. This axis will be a part of a support of the diffractometer.

An X-ray source having a comparatively short housing should preferably be used. Thus, a greater freedom of movement is obtained and the apparatus stability is also improved. It is particularly attractive to use an X-ray tube comprising a high-voltage connector which is constructed as a rotatable right-angle connector so that a cable portion does not necessary rotate when the tube is rotated but can occupy any arbitrary position.

A mechanism for permanently aiming the detector at the irradiated area during the rotation in a further preferred embodiment comprises a gearwheel transmission in order to ensure a non-slipping coupling between the $\theta$ rotation of the detector and the re-alignment thereof. A similar mechanism may be used for $\theta$ rotation of the X-ray source. Even more than for the $\psi$ movement it is attractive to use a stepping motor for the detector rotation which motor can also provide the re-alignment of the detector during rotation. Because the detector and the X-ray source do not move along a guide but about a real axis during the $\theta$ rotation, there is less direct mechanical restriction of the $\theta$ range.

A preferred embodiment comprises means for limiting the $\theta$ range for instance to avoid collision of moving parts and so on. Thereto the apparatus can be provided with an electronic circuitry by which the $\theta$ range, controlled by a drive mechanism and measured from a choosen fixed zero-position, is limited. A further embodiment includes a detector housing having a guide pin which cooperates with a support mounted on a detector rotation arm. For adjustment of an angular range a microswitch which is to be activated by the guide pin is mounted on the support, and this can be done due to the fact that the degree of the re-alignment is a function of the $\theta$ value.

In order to support the apparatus during a measuring process a further preferred embodiment utilizes a kind of three-point support. Two supporting points are situated at ends of a fixed limb which extends, viewed from the detector, behind the irradiation area, transversely to the plane of the vertical Seemann-Bohlin focussing circle. At each of the ends of this limb there is connected a further limb which is pivotable about the local connection point. Stable positioning of the apparatus can thus be achieved, even for measuring points which are not readily accessible.

In a preferred embodiment a third supporting point of the support is provided with a foot having a well defined end face which can be located at a fixed distance near to the area to be irradiated. The position of the area to be irradiated thus can be located and measured from the well defined end face.

Some preferred embodiments in accordance with the invention will be described in detail hereinafter with reference for the drawing, in which:

FIG. 1 diagrammatically shows the feasible movements and the beam path in an apparatus in accordance with the invention;

Figure 1:
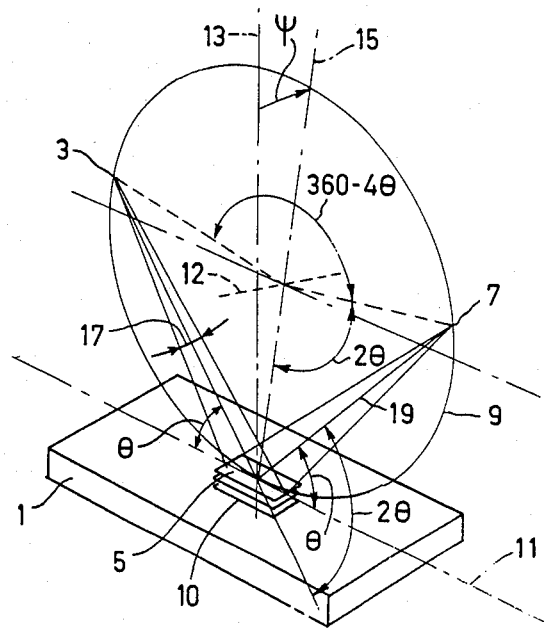

FIG. 1 shows an object 1 to be examined, together with a focus of the X-ray tube or radiation source 3, an irradiated area 5, and a detector entrance slit 7. The irradiated area 5, the radiation source 3 and the entrance slit 7 of the radiation detector are all situated on the circumference of a circle 9 which has already been referred as the Seemann-Bohlin focussing circle, and which will also be referred to as such hereinafter. In order to perform a stress measuring series, which is to be understood to mean a series of measurements of one interference line at different $\psi$ angles, it is possible to maintain the radiation source 3 and the irradiated area 5 on an object in a fixed position and to rotate the detector slit 7 over an angle $4\theta$. Alternatively, the irradiated area 5 of the object can be maintained in a fixed position, and the radiation source 3 and the detector slit 7 are rotated opposite to one another with each rotated over an angle $2\theta$. For a $\psi$ adjustment, the total Seemann-Bohlin arrangement 9 comprising the radiation source 3 and the detector slit 7 can be tilted about an axis 11 extending through the irradiated area 5. For the sake of clarity, the focussing circle 9 is tilted with respect to a perpendicular 13 to the object. If the perpendicular 13 coincides with the plane of the focussing circle 9, and thus with a central line 15 thereof, the condition $\psi=0$ holds. The advances of the $\psi$ measuring method over alternative methods are given in the article in Comptes rendus. As has been described there measurements through substantially larger $\psi$ angles are thus possible. A further advantage consists in that the penetration depth of an X-ray beam in the specimen varies less than in the $\omega$ method of measuring. A complete measurement performed in a measuring point involves, from 5 to 10 series of $\theta$ measurements between up to 60° on either side of the perpendicular situation of the Seemann-Bohlin circle over a $\psi$ range given by $-60°\leq\psi\leq+60°$. From an X-ray beam 17 of the X-ray source 3 a part 19 fulfilling the Bragg relation reaches the detector slit 7.

Figure 2:
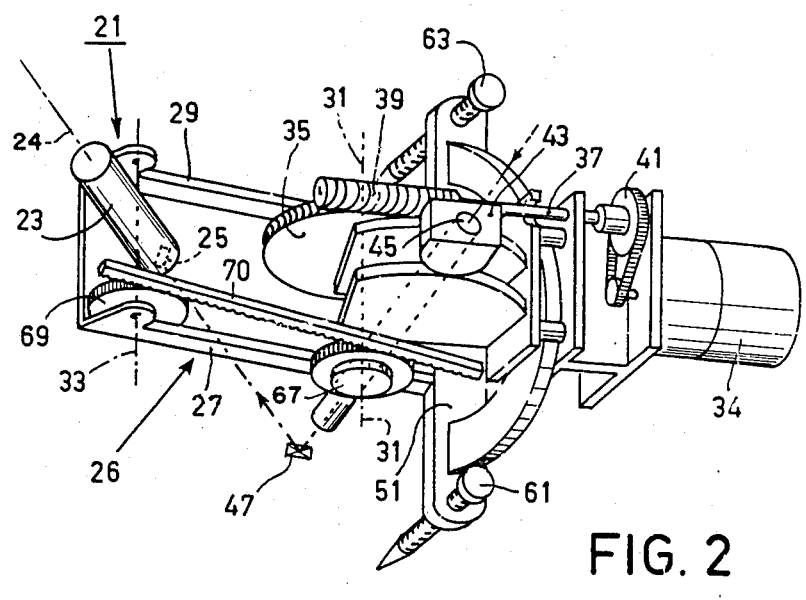
FIG. 2 is a more detailed representation of such an apparatus.

An embodiment of an X-ray examination apparatus in accordance with the invention is shown in FIG. 2. This apparatus comprises a detector holder 21 for a detector housing 23 with a detector entrance slit 25 which corresponds to the detector entrance slit 7 of FIG. 1. The detector holder 21 is supported by a double detector rotation support 26 which comprises arms 27 and 29. By the support 26, the detector is rotatable about a $\theta$ shaft 31 which extends transversely to the plane and through the center of the Seemann-Bohlin focussing circle. Consequently, this $2\theta$ motion can be quickly and accurately performed. For detector rotation the apparatus may comprise a d.c. motor or a stepping motor 34. A gearwheel 35 which is mounted about the shaft 31 on the detector rotation support 26 is drive by a worm-wheel drive 37, a worm-wheel 39, and a gear-wheel 41 which is driven by the motor.

A holder for an X-ray tube (omitted herein for the sake of clarity) may be mounted on a mounting surface 43. A radiation beam with a point-shaped focus to be generated in the X-ray tube is collimated, via a radiation duct 45, so as to form a desired irradiation area 47 which corresponds to the irradiated area 5 of FIG. 1.

A radiation focus of an X-ray tube is situated over the opening of the radiation duct 45, and the detector entrance slit 25 and the irradiation area 47 are all situated on the Seemann-Bohlin focussing circle shown in FIG. 1. The X-ray tube will further be described hereinafter with reference to FIG. 4; but for now only the importance of low weight and small dimensions are noted for an X-ray tube to be used. This is necessary in order to limit the weight of the apparatus, to increase its stability and to keep the freedom of movement of the source and the detector as high as possible.

A second drive motor can be used for pivoting the Seemann-Bohlin system. For performing this movement, the carrier for the X-ray tube comprises a circular guide which, when viewed in the apparatus, extends rectangularly to the plane through the Seemann-Bohlin focussing circle.

For positioning on or near an object to be measured, the apparatus is supported by a kind of a three-point support which comprises a first, fixed supporting limb 51 at the ends of which there are provided pivoting elements 53 and 55. To the ends of the fixed limb there are connected pivotable arms 57 and 59 having adjustable lengths and having ends remote from the connections which comprise adjustable supporting screws 61 and 63. To the limb 51 a fixed support with a supporting screw can be fixed relative to FIG. 4.

This support device offers stable positioning also for measuring points of an object to be measured which are not readily accessible. The pivotable limbs 57 and 59 may be adjusted so that the connecting line between the supporting points 61 and 63 is situated on the side of the fixed limb with respect to the irradiated area, such that at least one of the supporting points 61 and 63 is situated on a side of the fixed limb which is remote from the irradiated area. With a counter-weight connected to the apparatus measurements can also be executed together with providing a supporting area for the supporting points.

For optimum measurement it is desirable that a longitudinal axis 24 of the detector remains aimed at the irradiated area 47 over the entire $2\theta$ range.

When the detector is rotated for a $\theta$ measuring series, a detector axis 24 would perform an angular displacement with respect to a connecting line between the irradiated area and the detector slit if no additional steps were taken. This is because the detector rotates about the center of the Seemann-Bohlin circle and the irradiated area is situated on the circle circumference thereof. In order to maintain the detector aimed at the irradiated area during the $\theta$ rotation, a concentrally fixed, non-rotating gearwheel 67 is mounted about the rotary shaft 31. On a shaft 33 about which the detector housing 23 rotates during a $\theta$ scan, there is mounted a gearwheel 69 which comprises twice as many teeth as the gearwheel 67. Both gearwheels are coupled, for example, to a toothed rack 70 which transmits movements of the gearwheel 67 to the gearwheel 69 in a slip-free manner and which rotates the detector shaft back through half an angle of the $\theta$ motion. Consequently, the detector always remains aimed at the irradiated area for the present radiation optical system. Instead of using the transmission comprising a toothed rack, the detector can also be re-adjusted by means of one or more intermediate gearwheels, a chain transmission or a non-slipping belt transmission, a steel band and so on.

Figure 3:
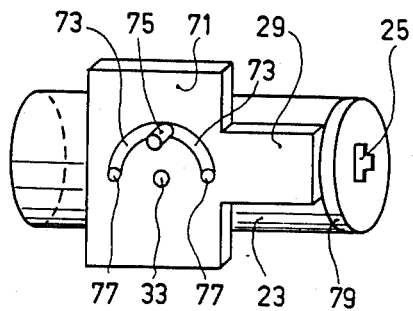
FIG. 3 shows an embodiment of a detector support for such an apparatus.

FIG. 3 shows the detector housing 23 with the detector entrance slit 25 and a part of the detector rotation arm 29. One end of the detector rotation arm 29 is formed by a supporting plate 71 in which the shaft 33 for the detector housing engages. In the plate 71 there is provided a slot 73 in which a guide pin 75 is movable together with the detector during rotation on the shaft 33. The guide pin 75 is connected to the detector housing and its position is adjustable by the re-adjustment of the detector which is a function of the $\theta$ rotation of the detector. An automatically limited $\theta$ path can be realised by mounting in the slot 73 microswitches 77 which are to be activated by the guide pin 75. Measurements in detector positions which are not allowed and collisions between parts of the apparatus during the measurement can thus be avoided. Preferably, at least one microswitch 77 is mounted to be displaceable with respect to the plate 71, thus enabling adjustment of a movement path for the detector. This safety mechanism can also be situated on an other part of the apparatus, such as directly connected to the axis of the shaft 31.

A frontportion 79 of the detector housing may be constructed as a diaphragm carrier in which exchangeable entrance diaphragms of different dimensions and shapes can be arranged. Such diaphragms can also be used for the formation of symmetrical intensity distribution from an assymetrical distribution of the X-rays, for example, due to the presence of $k\alpha 1$ as well as $k\alpha 2$ radiation in the X-ray beam. The entrance slit 25 shown in FIG. 3 has an appropriate shape in this respect. This kind of diaphragm is described in more detail in DE-B P No. 2,345,406 of Dr. Wolfstieg.

Figure 4:
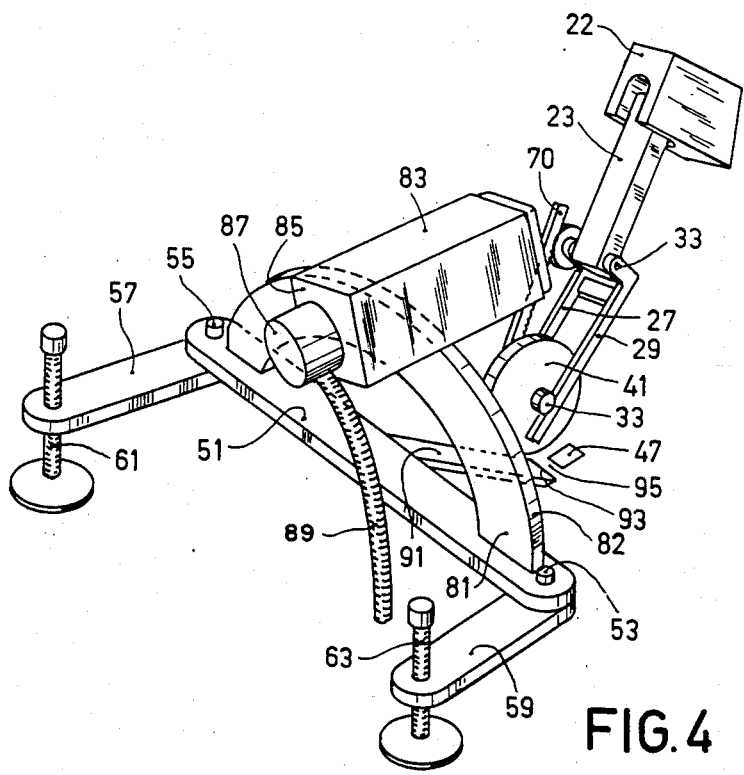
FIG. 4 shows an apparatus according to the invention, comprising an X-ray source and a detector, viewed from a different direction.

FIG. 4 shows the apparatus of FIG. 2, but now with an X-ray tube housing 83 and the detector housing 23 preferably with a pre-amplifier 22 and viewed from a different direction. The apparatus comprises a circular guide 81 which is rigidly connected to the supporting device and on which the X-ray tube 83 and the detector assembly can be displaced over an arc of a circle 82. During this displacement, the X-ray tube 83 with the radiation duct 45 in FIG. 2 and the detector rotation arms 27 and 29 with a detector housing 23 is tilted with respect to the supporting device.

The housing of the X-ray tube 83 is adapted to the apparatus in a sense that its length is reduced to, for example, 200 mm at the most. A window of the X-ray tube (not visible in the drawing) is situated in front of the radiation aperture 45 on the mounting surface 43 which may at the same time serve as a reference surface for focus positioning of the X-ray tube. For correct positioning, use can be made of a sensor which occupies an accurately defined position with repsect to the radiation focus in the tube and whereby the irradiated area 47 can be marked. In order to enhance the freedom of movement, the X-ray tube is mounted so that it can be switched over an angle of at least up to $\pm 90°$ in a preferred embodiment.

FIGS. 2 and 4 show an apparatus in which the X-ray is not motor driven. For movement by hand of the X-ray tube into a certain fixed Bragg-angle position the two following methods can be used. In order to keep the focus of the X-ray tube on the Seemann-Bohlin circle the radiation duct 45 together with two side pieces are provided with circle shaped position guides. The centers of these circles are the focus of the X-ray tube and the axis 31 respectively, the sum of the two radii being equal to the radius of the focussing circle. For $\theta$ adjustment one only has to ensure that the focus of the X-ray tube remains fixed on the focussing circle. Secondly, in order to make easy the otherwise necessity to direct the X-ray beam exactly onto the area to be irradiated scales can be provided on both positions guides or one can have fixed position indicators such as a scale or fixation pins thereon for a series of preferred and often used orientations. These positions can be fixed with aid of screws or pins which connect into locks provided in the tube housing in order to fix the position thereof. In a connection base 85 of the X-ray tube there can be inserted a high-voltage connector 87 which comprises a high-voltage cable 89 which is preferably fed out, side wise with respect to the X-ray tube. The cable 89 is freely rotatable by way of a socket portion. Consequently, when the X-ray tube is displaced along the guide 81, the cable can retain its position or it can rotate so that the freedom of movement of the X-ray is not impeded. The cable 89 is freely rotatable by way of a socket portion. Consequently, when the X-ray tube is displaced along the guide 81, the cable can retain its position or it can rotate so that the freedom of movement of the X-ray tube is not impeded. A third leg 91 of the support in this embodiment is provided with a well defined end face 93 which contacts the object to be measured in the measuring position at a fixed distance 95 from the irradiated area 47. With the aid thereof the irradiated area can easily be fixed and known by the user.

What is claimed is:

1. An X-ray examination apparatus comprising an X-ray source, an object receiving X-rays from said source, and an X-ray detector receiving X-rays from said object, the improvement comprising means for arranging said X-ray source, an irradiated area of said object, and a slit of said X-ray detector on a Seemann-Bohlin focusing circle, a mechanical shaft extending along a $\theta$ axis perpendicular to a focusing plane at the center of said Seemann-Bohlin focusing circle, said X-ray detector and a primary beam from said X-ray source being continually aimed at said irradiated area, and means for tilting said Seemann-Bohlin focusing circle transversely to said focusing plane about an axis through the center of said irradiated area to provide $\psi$ inclination.

2. An X-ray examination apparatus according to claim 1, wherein said X-ray detector is supported by a mechanical guide cooperating in a non-slipping manner with a first rotation guide, said first rotation guide being mounted on a device for rotatably supporting said X-ray detector, said mechanical guide cooperating with a second rotation guide concentrically mounted about said mechanical shaft for rotation of said X-ray detector.

3. An X-ray examination apparatus according to claim 2, wherein said first and second rotation guides are gearwheels having a 1:2 transmission ratio, said mechanical guide being a toothed rack.

4. An X-ray examination apparatus according to claim 2, wherein said mechanical guide includes at least one gearwheel cooperating with said first and second rotation guides.

5. An X-ray examination apparatus according to claim 1 or claim 2 or claim 3 or claim 4, wherein said X-ray detector is rotatably arranged in a housing about a rotation axis, said housing being mounted on a detector supporting arm for rotation with an abutment pin between at least one switching element to limit $\theta$ measuring ranges.

6. An X-ray examination apparatus according to claim 1 or claim 2 or claim 3 or claim 4, wherein a stepping motor rotates a supporting arm for said X-ray detector.

7. An X-ray examination apparatus according to claim 6, wherein said stepping motor controls redirection of said X-ray detector onto said irradiated area.

8. An X-ray examination apparatus according to claim 7, wherein said stepping motor provides movement of said X-ray source.

9. An X-ray examination apparatus according to claim 1 or claim 2 or claim 3 or claim 4, wherein said X-ray source is an X-ray tube of reduced length, said X-ray tube being mounted for disposition in said Seemann-Bohlin focusing circle and in directions transverse to said Seemann-Bohlin focusing circle.

10. An X-ray examination apparatus according to claim 9, wherein said X-ray tube includes a connector socket and a high voltage connection cable rotatable in said connector socket, said connection cable being directed at an angle of substantially 90° to said connector socket.

11. An X-ray examination apparatus according to claim 1 or claim 2 or claim 3 or claim 4, wherein said X-ray source, said object, and said X-ray detector are supported by a three-point support, said support including a fixed limb directed transversely to said Seemann-Bohlin focusing circle at said irradiated area, two limbs at ends of said fixed limb, two supporting points situated at ends of said two limbs, and a third supporting point fixed to a center portion of said fixed limb, said two limbs being movable at said ends of said fixed limb.

12. An X-ray examination apparatus according to claim 11, wherein said third supporting point is provided with an end face positioned at a fixed distance from said irradiated area.

13. An X-ray examination apparatus according to claim 1 or claim 2 or claim 3 or claim 4, wherein said X-ray source is provided with a first circular shaped position guide having a central point on a focusing point of said X-ray source and a second circular position guide being fixed to the center of said Seemann-Bohlin focusing circle, said first and second circular position guides having radii which have a sum equal to the radius of said Seemann-Bohlin focusing circle.

14. An X-ray examination apparatus according to claim 13, wherein at least one of said first and second circular position guides is provided with a plurality of fixing elements for a series of frequently used orientations.

15. An X-ray examination apparatus according to claim 1 or claim 2 or claim 3 or claim 4, wherein said X-ray detector is provided with a non-symmetrical diaphragm for converting asymmetrical distributions of X-ray beam intensities into a non-symmetrical distribution.

* * * * *